United States Patent [19]

Tummes et al.

[11] 3,935,285

[45] Jan. 27, 1976

[54] RECOVERY OF ALCOHOLS FROM ESTERS FORMED DURING AN OXO-SYNTHESIS

[75] Inventors: Hans Tummes, Oberhausen-Sterkrade-Nord; Jurgen Falbe; Boy Cornils, both of Dinslaken, all of Germany

[73] Assignee: Ruhrchemie AG, Oberhausen, Germany

[22] Filed: Sept. 18, 1972

[21] Appl. No.: 290,056

Related U.S. Application Data

[63] Continuation of Ser. No. 881,351, Dec. 2, 1969, abandoned.

[30] Foreign Application Priority Data

Dec. 27, 1968 Germany............................ 1817051

[52] U.S. Cl.......... 260/638 R; 260/542; 260/638 A; 260/638 HF; 260/643 B; 260/643 F
[51] Int. Cl.²...................................... C07C 29/00
[58] Field of Search...... 260/638 HF, 638 R, 638 A, 260/643 R, 643 F, 643 B, 542

[56] References Cited
UNITED STATES PATENTS

| | | | |
|---|---|---|---|
| 2,511,467 | 6/1950 | Gresham | 260/638 R |
| 2,595,096 | 4/1952 | Parker | 260/638 HF |
| 2,656,379 | 10/1953 | Mackenzie et al. | 260/643 R |
| 2,821,559 | 1/1958 | Habeshaw et al. | 260/638 HF |
| 3,260,683 | 7/1966 | Endler | 260/638 HF |
| 3,321,534 | 5/1967 | Landgraf et al. | 260/638 HF |
| 3,384,659 | 5/1968 | Bate | 260/643 F |
| 3,450,735 | 1/1969 | Lundeen et al. | 260/643 B |
| 3,462,500 | 8/1969 | Tummes et al. | 260/643 F |

*Primary Examiner*—Joseph E. Evans
*Attorney, Agent, or Firm*—Burgess, Dinklage & Sprung

[57] ABSTRACT

Alcohols are recovered from the ester-containing by-product from an oxo-synthesis, especially from the hydroformylation of propylene, by hydrolytically converting said by-product in the presence of water and a high surface area solid, such as an alumina at 250° to 350°C, and separating the alcohol from the material so converted. The converted product is preferably first hydrogenated prior to recovering the alcohol.

7 Claims, 1 Drawing Figure

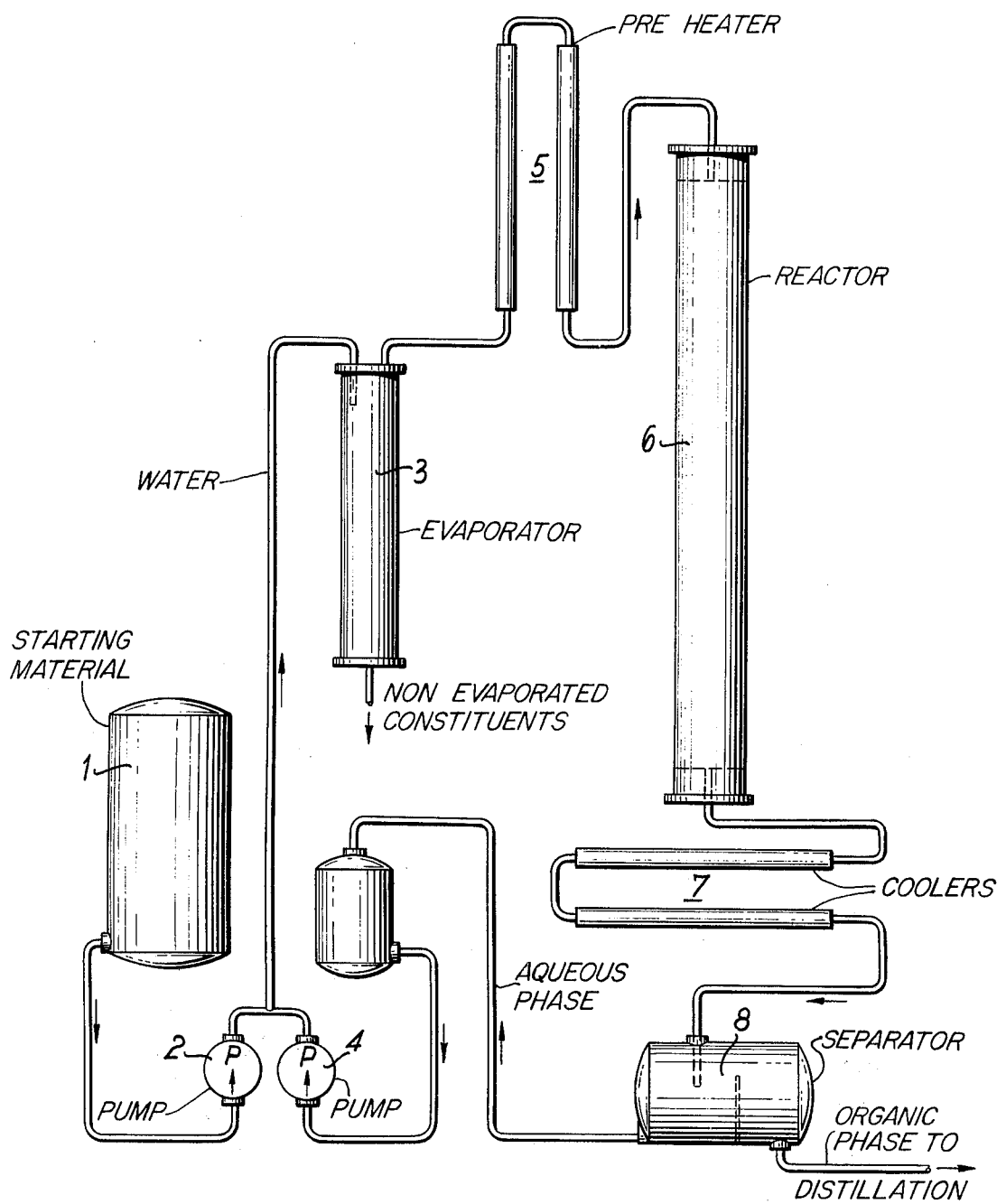

RECOVERY OF ALCOHOLS FROM ESTERS FORMED DURING AN OXO-SYNTHESIS

This is a continuation of application Ser. No. 881,351 filed Dec. 2, 1969 now abandoned.

PREAMBLE

In the oxo-reaction wherein aldehydes and alcohols are produced by the reaction of olefinically unsaturated compounds with carbon monoxide and hydrogen utilizing a catalyst based on cobalt, formic acid esters and higher boiling compounds are always formed as side products (see U.S. Pat. No. 2,779,794, column 3). The formic acid esters are generally derived from the alcohol resulting from the olefin used as starting material. The alcohol contains one carbon atom more than the olefin. Small amounts of formic acid esters of higher boiling alcohols are also formed.

Formic acid esters and higher boiling compounds are undesired side products of hydroformylation reactions since they needlessly consume part of the product alcohols and aldehydes and aggravate the recovery of the pure alcohols. Distillative separation of the alcohols and the formic acid esters derived therefrom is practically impossible due to the small difference of the respective boiling points and the formation of azeotropic mixtures of the compounds. However, distillative separation usually is the only technically practicable separation method for such reaction products since the esters must be removed before the fractionation of the alcohols.

Several processes have been hitherto described for removing formic acid esters from their admixtures with alcohols. Alcohols obtained by oxo-synthesis have been treated with mineral acids or an acid reacting salt of a mineral acid in order to improve their quality. Lewis acids, as for instance aluminum trichloride or boron trifluoride have also been used instead of mineral acids. These known processes, however, lead to a decrease of the alcohol yield and cause severe corrosion problems.

Oxo-alcohols have also been treated with alcoholic alkaline lyes to remove esters and other impurities therefrom and to improve their quality. However, stoichiometric amounts of alkali must be used and the alcohols must not contain significant amounts of aldehydes since the latter undergo undesired reactions in the presence of alkali and are thus lost as valuable products.

It is further known to remove formic acid esters from their mixtures with alcohols by thermal treatment with an aqueous solution of alakali salts of an organic acid at 200° to 260°C.

This process, however, requires the use of high pressures to avoid evaporation of water from the alkaline solutions as well as of low boiling constituents of the ester containing product. Furthermore, owing to the partial miscibility of the alcohols with water, costly measures are necessary to maintain the concentration of the aqueous alkaline solution constant.

The distillation residues remaining after the distillation of the aldehydes formed during the oxo-synthesis, especially in the case where propylene is used, have been thermally or catalytically split. This splitting procedure results usually in the exclusive formation of aldehydes, which can again be separated by distillation and united with the aldehydes obtained by distillation of the primary oxo-product. The residue remaining after the distillative separation of the aldehydes from the splitting product consists of unconverted esters and acetals primarily formed during the oxo-synthesis, from which small amounts of the corresponding alcohols can still be obtained. The working up of these esters and acetals requires several steps. The esters, after a preceding hydrogenation, must be saponified with alkali hydroxide solution and, thereafter, the alkaline saponification lye must be separated and the alcohols obtained by the saponification process isolated by distillation.

This splitting method is not suitable for the recovery of alcohols from esters admixed with the alcohols if — in contrast with the known process — not the recovery of aldehydes but that of alcohols is what is desired.

The present invention is a process for the production of alcohols from esters admixed with the alcohols, especially formic acid esters, as well as from products originating from reactions between aldehydes and alcohols, especially acetals.

According to this invention, such mixtures are treated with water at temperatures in the range of from 250° to 350°C, preferably from 280° to 320°C, and are thereafter distilled.

This process of this invention involves a hydrolysis reaction, which can be accelerated by substances having large surface areas, e.g. activated carbon or alumina. According to this invention, the hydrolysis of the esters, especially formic acid esters, with direct formation of alcohols by the treatment with water in the presence of alumina, is readily achieved in a very uncomplex manner and the recovery of the alcohols from the treated product requires only a distillation.

The formic acid esters are directly converted to alcohol and formic acid and the formic acid is spontaneously decomposed under the preavailing reaction conditions to $CO + H_2O$ or $CO_2 + H_2$ according to the equations:

1. $HCOOR + H_2O \rightarrow ROH + HCOOH$

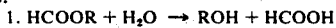
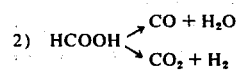

2) $HCOOH \begin{cases} CO + H_2O \\ CO_2 + H_2 \end{cases}$

Condensation products of aldehydes and alcohols simultaneously present in the product to be treated are likewise partially hydrolized during the process of this invention.

Thus, it is possible to markedly increase the yield of alcohols from a given amount of olefin if the process according to this invention is applied for the conversion of side products formed during the hydroformylation of olefins.

The excellent results obtained with the process of this invention by employing alumina as substance with a large surface area are surprising It is known that alumina in its different forms shows dehydrating activity and will, for instance, catalyze the conversion of alcohols to olefins. It would have been expected, therefore, that under the temperatures prevailing during the process of the invention the alcohols would be at least partially converted to olefins.

The presence of water in the present invention is mandatory for the realization of a high yield of alcohols. The undesired formation of olefins and ethers from the alcohols present is very substantially suppressed by the water and no decrease in the yield of valuable products results. Furthermore, the addition of water favors the hydrolytic cleavage of the higher boiling compounds to low molecular alcohols. An addition of water in an amount of from 2 to 20 percent by weight based on the starting material has proved to be most favorable. Addition of increased amounts of water does not influence the conversion but may impair the economy of the process because of the resulting increased energy requirements.

Several active clays differing in respect to their contents of CaO, $Na_2O$, $Fe_2O_3$, $SiO_2$ and thus in their pH values can be used as the active solid. The structures as well as the water contents of the aluminas employed can vary widely. For instance, an $Al_2O_3$ used in the process of this invention had the following composition (weight percent):

$Al_2O_3$ — 94%   $Na_2O$ — 0.5%   $SiO_2$ — 0.5%
CaO — 0.2%   $Fe_2O_3$ — 0.05%   $SO_3$ — 0.3%
balance: loss on calcining The aluminas need not necessarily be used in pure form, but can contain, besides impurities, binders and different additives.

The particular reaction temperature in the range of 250° to 350°C, preferably 280° to 320°C, is selected with regard to the facts that the reaction velocity decreases with temperature and the dehydration of the alcohols to olefins and ethers increases with temperature. The pressure used is low, usually in the range of 0 to 100 psig.

It is not necessary that the mixtures being treated encounter the active solid in vapor form. They can also be contacted therewith in liquid form with evaporation thereof occurring in the first layers of the solid and the conversion taking place in the following layers. Complete evaporation is not required, but high boiling constituents of the starting material can pass through the reactor in liquid form.

The feed is heated to the required temperature with the aid of an evaporator and a superheater connected in series before entering the reaction zone. Additional preheating, however, can occur in the heated reactor, as pointed out above.

Any product containing formic acid esters, preferably in admixture with alcohols and/or higher boiling condensation products from aldehydes and alcohols, can be used as starting material for the process of the invention. The present process has proved to be especially well suited for the conversion of mixtures containing formic acid esters, alcohols and higher boiling products obtained as residues after the distillation of the raw aldehydes from an oxo-synthesis. Especially favorable results are obtained if the starting material is a distillation residue remaining after the distillative separation of the isomeric butyraldehydes from a hydroformylation product derived from propylene. The mixture treated according to this invention is worked up by fractionation, preferably after a preceding hydrogenation, whereby $C_4$-alcohols of high quality are obtained. The entire product as well as distinct fractions thereof can be hydrogenated. The hydrogenation can be performed in known manner in gaseous as well as in liquid phase in the presence of conventional hydrogenation catalysts. The recovery of pure alcohols by fractionation of the hydrogenation product is also conducted in known manner in several stages, with prerunnings, containing low boiling impurities besides pure alcohols being separated in the first stage.

As hereinbefore mentioned, the distillative recovery of pure alcohols prepared by the oxo-synthesis is only possible after preceding removal of the formic acid esters. In comparison to known processes the process according to the invention is superior in certain respects. For instance, since it is operated at ordinary atmospheric pressure it requires only small investments and it is characterized by low material costs because the active solid used is cheap and the losses thereof in the process are small. High yields of valuable products can be obtained by the practice of the process of this invention.

THE DRAWING

A continuous process according to the invention is schematically illustrated in the attached drawing.

Starting material containing formic acid ester and higher boiling compounds from vessel 1 is introduced via pump 2 to evaporator 3 heated to about 300°C. An amount of water equal to about 10 weight percent depending on the nature of the starting material is simultaneously introduced to evaporator 3 via pump 4. The vapors exiting from evaporator 3 are heated in preheater 5 to 300°C and introduced from above into tube reactor 6, containing alumina, also heated to 300°C with the aid of a heating medium. Non-evaporated constituents of the product are discharged from the lower part of the evaporator. The vapors exiting from tube reactor 6 are condensed in cooler 7 and separated from water in a phase separator 8. The organic phase is led to a distillation unit for further processing, while the aqueous phase is recirculated to evaporator 3.

To keep the energy requirements as low as possible, the heat supplied to the product during the evaporation and conversion can be recovered during the following condensation with the aid of heat exchangers and used for the heating of the starting materials.

Instead of tube reactor 6 a shaft furnace filled with alumina can be used.

EXAMPLES

EXAMPLE 1

1 liter of a product of the following composition (weight percent):
9.1% i-butylformate
18.9% n-butylformate,
10.9% i-butanol,
19.8% n-butanol,
42.0% higher boiling condensation products
obtained from the hydroformylation product of propylene after separation of i- and N-butyraldehyde, was (with reference to the drawing) jointly evaporated with 100 ml water per hour in an evaporator heated to 300°C. The vapors were introduced from above in a heated tube (diameter 30 mm; length 1.4 m) filled with alumina. The tube was maintained at 300°C by means of a heating medium. The hydrolysis-product exiting from the bottom of the tube was condensed and cooled to 20°C. The liquid product thereby obtained (about 1 liter hour) had the following composition:
4.8% i-butyraldehyde 17.8% i-butanol
10.2% n-butyraldehyde 36.4% n-butanol
1.5% butylformate 21.2% higher boiling condensation products
1.1% dibutylether 7.0% water

EXAMPLE 2

An apparatus as described in Example 1, containing $Al_2O_3$ as the active solid, was charged with 150 ml water per hour and 1 liter of a product obtained by hydroformylation of isobutene followed by distillative separation of the resulting $C_5$-aldehydes. The temperature in the reactor was 310°C. From the comparison of the composition of the starting material and the hydrolysis product set out below it is seen that a substantially high regeneration of alcohols from the esters and the high boiling constituents was effected.

|  | Composition (weight percent) | |
|---|---|---|
|  | Feed | Hydrolysis product |
| i-butene | 0.1 | 1.0 |
| $C_5$-aldehydes | 0.4 | 7.0 |
| $C_5$-formic acid esters | 22.3 | 0.9 |
| $C_5$-alcohols | 39.5 | 59.8 |
| thick oil | 37.7 | 31.3 |

EXAMPLE 3

From a decobalted product obtained by hydroformylation of diisobutylene, comprising $C_8$-hydrocarbons, $C_9$aldehydes, $C_9$-alcohols, formic acid esters derived from $C_9$-alcohols as well as higher boiling condensation products of $C_9$-aldehydes and $C_9$-alcohols: $C_8$-hydrocarbons and $C_9$-aldehydes were separated by distillation and a bottom product of the following composition remained:

45% $C_9$-alcohols
15% formic acid esters of the $C_9$-alcohols
40% higher boiling condensation products 1 kg of this mixture was passed together with 10 percent water at 300°C from above to the bottom through the reaction tube filled with alumina of an apparatus as described in Example 1. The product resulting from the said splitting consisted of:

65% $C_9$-alcohol
2% formic acid esters of the $C_9$-alcohols
33% higher boiling condensation products It was hydrogenated in the presence of a nickel catalyst in liquid phase at 140°C and 100 atmospheres gauge and fractionated.

Sixty-five percent of the starting mixture subjected to hydrolysis was obtained in form of pure $C_9$ alcohols.

Without the preceding treatment according to this invention only 55 percent of the starting mixture were obtained in the form of $C_9$-alcohols after hydrogenation and distillation of the bottom product.

EXAMPLE 4

1 liter of a reaction product of the hydroformylation of propylene of the following composition:

7.7% i-butyliformate,
15.5% n-butylformate,
9.0% i-butanol,
17.3% n-butanol,
50.5% higher boiling condensation products was passed from above to the bottom through a reaction tube as hereinbefore described in Example 1 but filled with activated carbon in granular form. Ten percent water was added and the temperature maintained at 300°C. The reaction product obtained after the treatment according to the invention had the following composition:

3.4% i-butyraldehyde,
10.2% n-butyraldehyde,
2.3% butylformate,
1.3% dibutylether,
13.3% i-butanol,
41.3% n-butanol,
21.1% higher boiling condensation products
7.1% water

We claim:

1. In a process for recovering an alcohol from an ester formed by the hydroformylation of an olefinically unsaturated compound with carbon monoxide and hydrogen, the improvement comprising heating the said ester with 2 to 20 % by weight water based on the combined weight of a distillation residue obtained by a distillative separation of aldehyde products from the raw product resulting from said hydroformylation, said products containing formic acid esters in admixture with alcohol and/or higher boiling condensation products from aldehydes and alcohols, at a temperature in the range of 250° to 350°C and passing the heated product in the vapor phase at ordinary atmosphereic pressure over a high surface area porous solid alumina or activated carbon maintained at said temperature and separating and recovering the resulting alcohol product from gaseous products.

2. A process according to claim 1 wherein the porous solid material is alumina.

3. The process of claim 1 wherein said ester is present in a mixture with alcohols, said mixture including formic acid esters, acetals and higher boiling compounds obtained as distillation residue after distillative separation of aldehyde products from the raw product resulting from a hydroformylation of an olefin.

4. The process of claim 3 wherein said mixture is the distillation residue obtained after distillative separation of the isomeric butyraldehydes from the raw product resulting from the hydroformylation of propylene.

5. A process comprising:
   a. preparing a raw oxo product by the hydroformylation of an olefin;
   b. separating aldehyde from said raw oxo product, leaving an ester, alcohol and acetal-containing residue;
   c. hydrolytically converting said residue in the presence of water in the range of 2 to 20 weight percent water based on said residue over a particulate porous solid of alumina or activated carbon having a high surface area and at a temperature in the range of 250° to 350° and at ordinary atmospheric pressure; and
   d. separating the so converted product to recover an alcohol having one more carbon atom than said olefin.

6. The process of claim 5 comprising catalytically hydrogenating said converted product prior to said separating.

7. The process of claim 6 wherein said olefin is propylene, said ester is butylformate and said alcohol is butanol.

* * * * *

UNITED STATES PATENT OFFICE
CERTIFICATE OF CORRECTION

Patent No. 3,935,285          Dated January 27, 1976

Inventor(s) Hans Tummes et al.

It is certified that error appears in the above-identified patent and that said Letters Patent are hereby corrected as shown below:

Column 2, line 37, before "according" -- $H_2$ -- should be inserted.

Signed and Sealed this

Sixth Day of July 1976

[SEAL]

Attest:

RUTH C. MASON
*Attesting Officer*

C. MARSHALL DANN
*Commissioner of Patents and Trademarks*